(12) United States Patent
Li et al.

(10) Patent No.: US 11,149,071 B2
(45) Date of Patent: *Oct. 19, 2021

(54) FUSION PROTEIN SLIT2D2(C386S)-HSA AND USE THEREOF IN PREVENTION AND/OR TREATMENT OF LUNG INFLAMMATION

(71) Applicant: Asclepius (Suzhou) Technology Company Group Co., Ltd., Suzhou (CN)

(72) Inventors: Huashun Li, Suzhou (CN); Baoyong Ren, Suzhou (CN); Peng Liu, Suzhou (CN)

(73) Assignee: ASCLEPIUS (SUZHOU) TECHNOLOGY COMPANY GROUP CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,186

(22) Filed: Nov. 21, 2019

(65) Prior Publication Data

US 2020/0087362 A1 Mar. 19, 2020

Related U.S. Application Data

(63) Continuation of application No. PCT/CN2018/086548, filed on May 11, 2018.

(30) Foreign Application Priority Data

May 26, 2017 (CN) .......................... 201710387439.8

(51) Int. Cl.
| | |
|---|---|
| *A61K 38/00* | (2006.01) |
| *C07K 14/47* | (2006.01) |
| *A61P 11/06* | (2006.01) |
| *A61P 29/00* | (2006.01) |
| *C07K 14/765* | (2006.01) |

(52) U.S. Cl.
CPC .......... *C07K 14/4702* (2013.01); *A61P 11/06* (2018.01); *A61P 29/00* (2018.01); *C07K 14/765* (2013.01); *A61K 38/00* (2013.01); *C07K 2319/31* (2013.01)

(58) Field of Classification Search
CPC .............. C07K 14/4702; C07K 14/765; C07K 2319/31; A61P 11/06; A61P 29/00; A61K 38/00
See application file for complete search history.

(56) References Cited

U.S. PATENT DOCUMENTS

| | | | | |
|---|---|---|---|---|
| 4,959,314 A * | 9/1990 | Mark | ............. | C07K 14/525 424/85.2 |
| 2007/0026013 A1* | 2/2007 | Rosen | ............. | A61P 15/00 424/192.1 |
| 2012/0129757 A1* | 5/2012 | Li | ............. | A61P 9/00 514/1.1 |
| 2014/0073564 A1* | 3/2014 | Madsen | ............. | C07K 14/62 514/5.9 |
| 2014/0073565 A1* | 3/2014 | Kevil | ............. | G01N 33/564 514/6.9 |
| 2016/0120940 A1 | 5/2016 | Robinson et al. | | |
| 2019/0309050 A1* | 10/2019 | Li | ............. | A61K 9/08 |

FOREIGN PATENT DOCUMENTS

| | | |
|---|---|---|
| CN | 101687014 A | 3/2010 |
| CN | 102083452 A | 6/2011 |
| CN | 104271197 A | 1/2015 |
| CN | 106279423 A | 1/2017 |
| CN | 106543278 A | 3/2017 |
| CN | 106589130 A | 4/2017 |
| CU | 106543278 A | 3/2017 |
| WO | 2005/000098 A2 | 1/2005 |
| WO | 2017/063185 A1 | 4/2017 |

OTHER PUBLICATIONS

Moldoveanu et al. Inflammatory mechanisms in the lung. 2009. J Inflamm Res. 2009; 2: 1-11 (Year: 2009).*
Prasad et al. Pivotal Advance: Slit-2/Robo-1 modulates the CXCL12/CXCR4-induced chemotaxis of T cells. 2007. Journal of Leukocyte Biology vol. 82, Sep. 2007 (Year: 2007).*
Pilling et al. Fibroblasts secrete Slit2 to inhibit fibrocyte differentiation and fibrosis. PNAS Dec. 23, 2014 111 (51) 18291-18296 (Year: 2014).*
International Search Report for Application PCT/CN2018/086548.
Written Opinion of the International Searching Authority for Application PCT/CN2018/086548.
Structural insight into Slit-Robo signalling, Erhard Hohenester, Department of Life Sciences, Imperial College London, London SW7 2AZ, U.K., Biochemical Society Annual Symposium No. 75, Biochem. Soc Trans. (2008) 36, 251-256; doi:10.1042/BST0360251.
Study on expression level changes of axon guidance cues Slit2 and Robo4 in lung tissue of rat with acute lung injury, Abstract, Postgraduate: Li Lin (Cardiology), Directed by: Professor Qing Guo-Zhong, Key Words: Slit2; Robo4; acute lung injury; Sepsis; endothelial permeability; Title of the item: Medicine and Health Technology, 1st issue, Date: Jan. 15, 2014, pp. E063-22.
The State Intellectual Property Office of People's Republic of China, 100102, Application No. or Publication No. 201710387439.8, Applicant of Patentee: Suzhou SiLi Biotechnology Co., Ltd., Title of Invention: Recombinant Slit2D2 (C3865)-HSA fusion protein and application thereof in preventing and/or treating pulmonary inflammation, Document number or Document title: CN 106543278A & CN 106589130A, publication date (or application date of the conflicting: Mar. 29, 2017 & Apr. 26, 2017.

* cited by examiner

*Primary Examiner* — James H Alstrum-Acevedo
*Assistant Examiner* — Mercy H Sabila
(74) *Attorney, Agent, or Firm* — Flener IP & Business Law; Zareefa B. Flener

(57) ABSTRACT

The present invention provides a recombinant fusion protein. The fusion protein is formed by the fusion of D2 domain of Slit2 protein and HSA protein, and the position 386 amino acid of the Slit2 protein molecule is serine.

3 Claims, 5 Drawing Sheets

Specification includes a Sequence Listing.

FUSION PROTEIN SLIT2D2(C386S)-HSA AND USE THEREOF IN PREVENTION AND/OR TREATMENT OF LUNG INFLAMMATION

CROSS-REFERENCE TO RELATED APPLICATION

This application is a continuation application of International patent application No. PCT/CN2018/086548, filed on May 11, 2018, which claims the benefit and priority of Chinese patent application No. CN201710387439.8, filed on May 26, 2017, each of which is incorporated herein by reference in its entirety and for all purposes.

FIELD OF THE INVENTION

The present invention relates to the field of biomedical technology, in particular to a recombinant fusion protein Slit2D2(C386S)-HSA and use thereof in the treatment and/or prevention of lung inflammation.

BACKGROUND OF THE INVENTION

In recent years, with the continuous improvement of health level, infectious diseases are no longer the most important cause of endangering human health. However, the harm of serious chronic diseases including tumors, autoimmune diseases, and vascular diseases have gradually become the primary hazard. But the related diseases represented by lung inflammation diseases are seriously affecting human health, including acute inflammation and chronic inflammation.

Acute lung injury (ALI)/Acute respiratory distress syndrome (ARDS) is an acute lung inflammation, which is caused by various pulmonary factors and extrapulmonary factors that is a clinical syndrome characterized by acute respiratory distress, non-cardiac Pulmonary edema and persistent over-inflammatory response. ARDS has now become an important cause of severe trauma, severe infections, and death in elderly patients. The research results have shown that the mortality rate of ARDS is as high as 22%, and the mortality rate of elderly patients over 85 years old is as high as 60%. In recent years, although there has been some progress in the pathogenesis, diagnosis and treatment, the recovery rate of young ARDS patients has improved, but their lung function and quality of life cannot restore to normal levels that cause a heavy physical and psychological burden on patients with ARDS.

In addition, asthma is an important global chronic lung inflammation disease. According to a report released by the China Asthma Alliance, there are as many as 30 million asthmatics in China, and the prevalence of asthma in the population is as high as 1.24%, but in the many asthmatics, children account for 6 million, and the prevalence rate is 1.97%, it means that there are 2 asthmatics per 100 children. There are approximately 334 million people with asthma and 328 million people with COPD worldwide. It is expected that COPD will become the third deadly disease in the United States in 2030. The essence of asthma is an airway inflammatory chronic disease caused by allergens. Compared with the airway structure of normal people, asthmatics not only have airway inflammation, but also have airway remodeling including goblet cell hyperplasia, sub-epithelial fiber deposition, smooth muscle hyperplasia and hypertrophy, and vascular proliferation. The process of airway remodeling is closely related to the severity of the disease. Clinically, the main symptoms of asthma attacks are cough and chest pain, difficulty breathing, and paroxysmal wheezing. The majority patients can be self relieved or be relieved by treatment, but if they are not controlled in time, and serious asthma can even be life-threatening. The severity and frequency of asthma attacks vary from person to person. Chronic inflammation and remodeling of tissue structure lead to the important pathophysiological features of diseases, such as persistent airway hyperresponsiveness. At present, the drugs for treating asthma in clinical application mainly include two major types. One type is a control drug, which need to be used daily, long-term or even for lifetime, and primarily control asthma attacks and their further development through anti-inflammatory effects. These drugs include inhaled corticosteroids, leukotriene regulators, long-acting beta 2 receptor agonists, anti-IgE antibodies, and the like. Another type is a relief drug that relieves the symptoms of acute asthma attacks by quickly releasing bronchospasm. These drugs including rapid-acting inhaled 132 receptor agonists, inhaled anticholinergic drugs, etc., mainly through the action of cell surface 132 receptors of cell membranes of airway smooth muscle and mast cells etc., relax airway smooth muscle, reduce the release of mast cells, alkalophilic Granulocyte degranulation and inflammatory mediators, decrease the permeability of microvascular, and increase the swing of airway epithelial cilia and so on, thus alleviate asthma symptoms. The current drugs are effective in reducing the frequency and symptoms of asthma attacks, but these drugs only treat symptoms, not cure the underlying problem, and can't ultimately cure asthma. Once the drugs are stopped, the patient's condition will be recurred and worsen. If airway remodeling and persistent lung function loss have been established, it cannot be reversed by the current medical methods. In addition, a considerable proportion of patients is not sensitive to the existing anti-inflammatory therapies and will develop into severe refractory asthma. Facing the aforementioned lung inflammation, it is of great significance to develop highly effective anti-inflammatory drugs.

Slit is a type of secreted glycoprotein with a molecular weight of about 200 kD. The gene of Slit cloned in mammals has three members, Slit1, Slit2 and Slit3, which is composed of an N-terminal signal peptide, four leucine-rich repeats (LRRs) and multiple EGF-like repeats (7 in *Drosophila* and 9 in vertebrates); studies have shown that the LRRs are the binding regions of Slit protein and receptor Robo. The Slit protein plays a role by Robo binding receptor. The extracellular IgG domains of Robos are thought to be required for binding to Slit ligand. The longer intracellular region interacts with some important signaling molecules and participates in the signal transduction downstream of Slit/Robo, thereby complete the transmission of stimulation signal from the outside of cell to internal skeleton. At present, the mechanism analysis of the protein in the Slit-Robo interaction region has been confirmed in some literature, and found that the second domain D2 of Slit2 binds to Ig1 of Robo1, thereby initiates signal transduction (Morlot, Hemrika et al. 2007, Hohenester 2008, Seiradake, von Philipsborn et al. 2009). Slit2 molecule has anti-inflammatory ability and has potential application value in inflammatory diseases (201510661923.6, PCT/CN2015/092079, 201611110752.9, US20160120940).

SUMMARY OF THE INVENTION

In view of this, the present invention provides the following technical solutions.

An aspect of the present invention provides a fusion protein, which comprises D2 domain of Slit2 protein and HSA, wherein the cysteine in the Slit2D2, corresponding to the position 386 of the Slit2 protein, is mutated to serine.

Illustratively, the present invention provides a fusion protein having the following structure: Slit2D2 (C386S)-HSA, or HSA-Slit2D2 (C386S), wherein "-" represents a chemical bond or a linker.

Another aspect of the present invention provides a fusion protein, which consists of a D2 domain of a Slit2 protein and HSA, wherein the cysteine in the D2 domain of Slit2 protein, corresponding to the position 386 of the Slit2 protein, is mutated to serine. Illustratively, the present invention provides a fusion protein having the following structure: Slit2D2 (C386S)-HSA, or HSA-Slit2D2 (C386S), wherein "-" represents a chemical bond or a linker.

Preferably, the fusion protein provided by the invention can be formed by fusion of the D2 domain of Slit2 protein and the HSA protein, wherein the cysteine in the D2 domain of Slit2 protein, corresponding to the position 386 of the Slit2 protein, is mutated to serine.

Illustratively, the D2 domain of Slit2 protein comprises or consists of the amino acid sequence as shown in SEQ ID NO: 1.

Preferably, the fusion protein of the present invention comprises or consists of the sequence as shown in SEQ ID NO: 2.

The present invention also provides a nucleotide encoding the above fusion protein, the nucleotide sequence comprises or consists of the sequence as shown in SEQ ID NO: 3.

Yet the present invention also provides a expression cassette comprising the nucleotide.

The present invention also provides a vector (for example, plasmid or viral vector), or microorganism (for example, *Escherichia coli, Bacillus subtilis, Bacillus megaterium, Corynebacterium, Saccharomyces cerevisiae, Pichia* and yeast, etc.), or a recombinant cell (for example, plant or animal cells) that comprises the nucleotide encoding the fusion protein.

The present invention still provides a preparation method of the fusion protein, including expressing the fusion protein encoded by the nucleotide sequence.

Optionally, the preparation method of the fusion protein includes the following steps:

(1) constructing a recombinant expression vector including the nucleotide encoding the fusion protein;

(2) transforming the prepared recombinant expression vector into a host cell or microorganism, and expressing the fusion protein encoded by the nucleotide;

(3) isolating and purifying the fusion protein.

In the present invention, the recombinant expression vector is preferably a plasmid vector, and the host cell or microorganism is preferably selected from the group consisting of *Escherichia coli, Bacillus subtilis, Bacillus megaterium, Corynebacterium, Saccharomyces cerevisiae, Pichia* or mammalian cells. Specifically, the expression vector is preferably used a pCDNA3.4 in the present invention, the host cell or microorganism is *Escherichia coli* TOP10, or the isolation and purification of the fusion protein are performed by affinity chromatography and/or ion exchange chromatography.

The present invention also provides a pharmaceutical composition comprising the fusion protein and a pharmaceutically acceptable excipient.

The present invention also provides the use of the fusion protein for the preparation of a pharmaceutical composition for preventing and/or treating of lung inflammation. In the present invention, lung inflammation includes acute chronic lung inflammation diseases and chronic lung inflammation diseases such as acute lung injury or asthma etc.

In the present invention, the cysteine corresponding to the position 386 of the Slit2 sequence is substituted to serine by a genetic engineering method. This substitution unexpectedly increases its stability in vivo, prolongs its half-life, and improves its therapeutic effect on lung inflammation, and its therapeutic effect is significantly more effective than the Slit2D2-HSA recombinant protein. The preparation process is easy to purify and separate, and its purity as high as 97.48%, which is better for the developing, spreading and applying of drugs.

The fusion protein provided by the present invention may have at least one of the following effects: Preventing and/or treating acute lung inflammation by significantly inhibiting the inflammatory cells from infiltrating into lung. Preventing and/or treating chronic lung inflammation by inhibiting the infiltration of inflammatory cells in the alveoli and inhibiting the expression of inflammatory factors, protecting lung respiratory function and achieving significant effects.

DETAILED DESCRIPTION OF THE INVENTION

The technical solutions in the embodiments of the present invention will be clearly and completely described in the following with reference to the accompanying drawings in the embodiments of the present invention. It is apparent that the described embodiments are only a part of the embodiments of the present invention, and not all of the embodiments. All other embodiments obtained by those skilled in the art based on the embodiments of the present invention without creative efforts are within the scope of the present invention.

Example 1 Preparation of the Fusion Protein Slit2D2(C386S)-HSA

Figure 1:
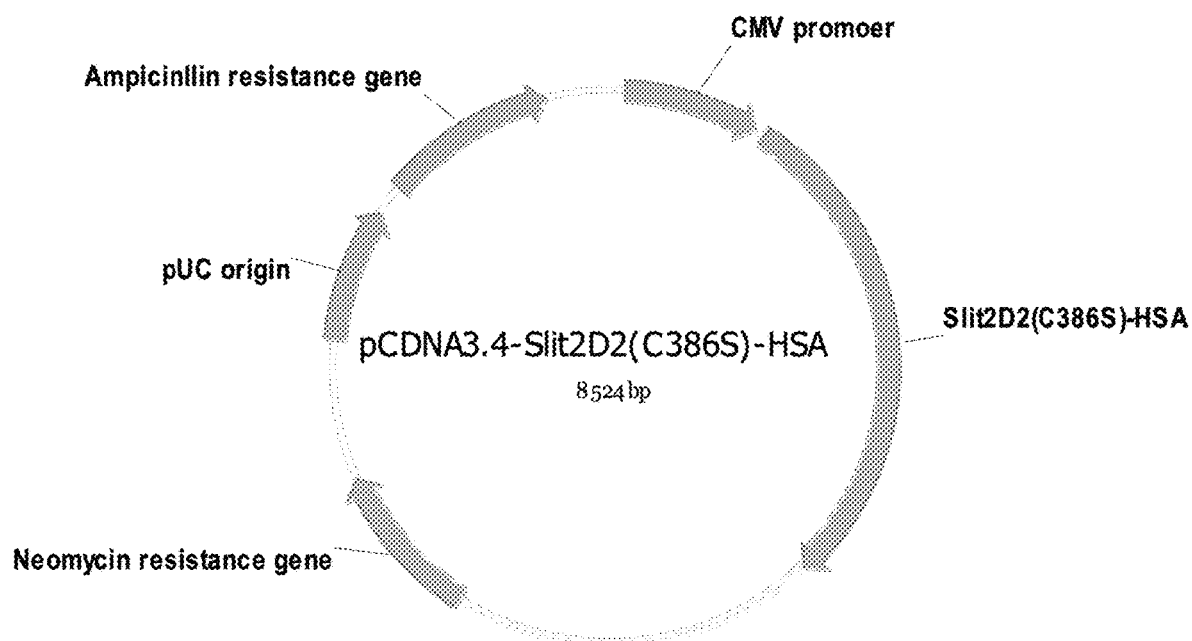
FIG. 1 illustrates a map of the recombinant plasmid pCDNA3.4-Slit2D2(C386 S)-HSA of the recombinant Slit2D2(C386S)-HSA fusion protein provided by the embodiments of the present invention.

Based on the known Slit2 sequence [GenBank: EAW92793.1], the second domain of Slit2 was analyzed, designed and constructed, and Slit2D2(C386S) was designed as shown in SEQ ID NO: 1, and further, the sequence of Slit2D2(C386S)-HSA fusion protein and the encoding gene of Slit2D2(C386S) were designed as shown in SEQ ID NO: 2 and SEQ ID NO: 3, respectively. The fusion gene fragment of Slit2D2(C386S)-HSA was obtained by total gene synthesis, and inserted into pCDNA3.4 (Brand: Thermo, Art. No.: A14697) expression vector by T/A clone. The map of the recombinant vector pCDNA3.4-Slit2D2(C386S)-HSA is shown in FIG. 1. The above recombinant expression vector was transformed into *E. coli* TOP10, and then inoculated into a solid medium containing ampicillin (AMP) for propagation. Positive clones were screened, and the vector was confirmed to be successfully constructed by sequencing, and preserved.

The recombinant plasmid in *E. coli* TOP10 was extracted with an endotoxin-free plasmid extraction kit for transfection into ExpiCHO-S™ cells (Gibco Catalog No. A29127). ExpiCHO-S™ cells were cultured and transfected with the recombinant plasmid when the cell density reached $4\times10^6\sim6\times10^6$ cells/ml (Transfection reagent: Expi-Fectamine™ CHO Transfection Kit, Gibco Catalog No. A29129). After transfection, the cells were cultured for 10 days. The supernatant was collected, centrifuged at high speed, and purified through a HSA affinity chromatography (Filler of chromatography: Thermo, Art. No.: 191297050) and a weak anion exchange chromatography (Brand: Smart-Lifesciences, Art. No.: DEAE Beads 6FF, SI005025) to purify the Slit2D2(C386S)-HSA fusion protein.

Figure 2:
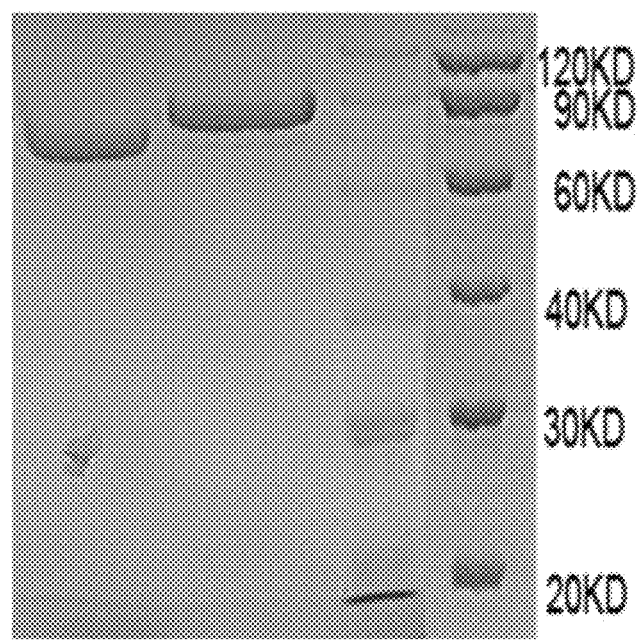
FIG. 2 illustrates a SDS-PAGE diagram showing the molecular weight detection of the Slit2D2(C386S)-HSA fusion protein provided by the embodiments of the present invention.
Figure 3:
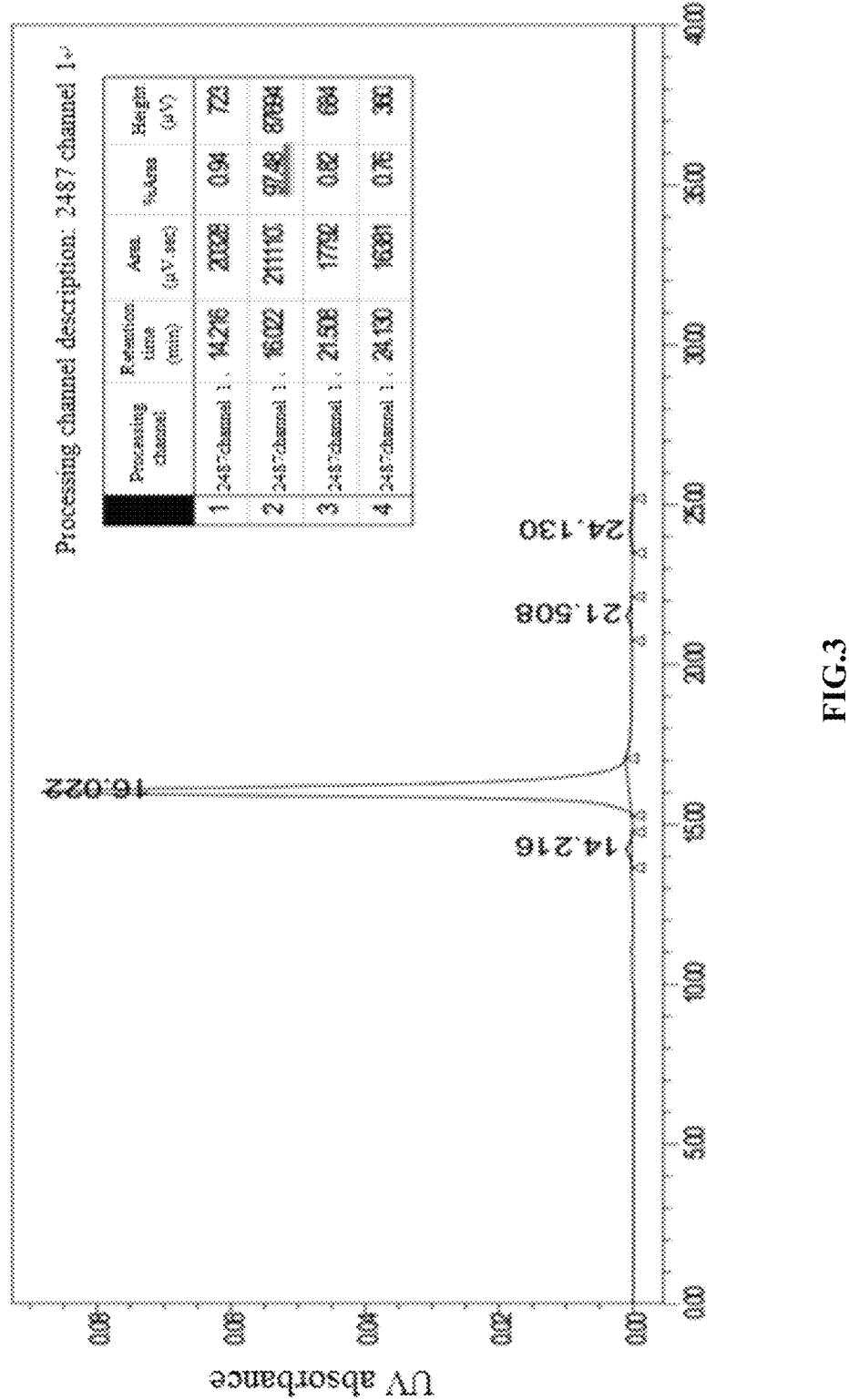
FIG. 3 illustrates a SEC-HPLC detection spectrum of the Slit2D2(C386S)-HSA fusion protein after purification provided by the embodiments of the present invention.

FIG. 2 is a SDS-PAGE diagram showing the molecular weight detection of the Slit2D2(C386S)-HSA fusion protein. FIG. 3 is a SEC-HPLC detection spectrum of the Slit2D2(C386S)-HSA fusion protein after purification. The molecular weight of the purified fusion protein was determined by SDS-PAGE method, and the purity of the fusion protein was detected by SEC-HPLC. It can be seen from FIG. 2 and FIG. 3 that the recombinant expression vector expressing the fusion protein Slit2D2(C386S)-HSA has been successfully constructed, and the fusion protein Slit2D2(C386S)-HSA was expressed and purified in the host cell, and its purity was up to 97.48%.

Example 2 Pharmacodynamic Detection of the Fusion Protein Slit2D2(C386S)-HSA in Rat Model of Acute Lung Injury Acute lung injury (ALI) is a systemic uncontrolled inflammatory response caused by various direct and indirect injury factors, accompanied by alveolar epithelial cells and capillary endothelial cell injury, its pathogenesis is still unclear, and there is still no effective treatment means. A rat model with airway infusion of lipopolysaccharide (LPS) is a commonly used animal model. In this study, airway infusion of LPS induced acute lung injury in rats. The animals were injected compounds via tail vein. After four hours, lung lavage and bronchoalveolar lavage fluid were collected, and differential cell were counts and measured to represent the efficacy of test compounds in preventing lipopolysaccharide-induced lung injury.

2.1 Experimental Animals
Animal: Wistar rat
Prior treatment: no
Gender: male
Body weight: 220-250 g;
Breeder/supplier: Beijing Weitong Lihua Experimental Animal Co., Ltd.
Testing facility: Shanghai PengLi Biological Company
Adaption: not less than 7 days
Room: SPF room
Room temperature: 20-26° C.
Relative humidity of room: 40-70%
Photoperiod: 12 hours of light (08:00-20:00) and 12 hours of darkness
Animal feeding: Treatment group 3~4/cage 2.2 Animal Grouping and Dosage Regimen
The test design and dosage regimen of animal grouping are shown in Table 1.

TABLE 1

Animal grouping and dosage regimen

| Group | Test substance | Number of rats | Routes of administration | Concentration mg/mL | Dosage mL/kg | Dosage mg/kg | Dosage regimen |
|---|---|---|---|---|---|---|---|
| 1 | PBS | 6 | i.v. | N/A | 2.5 | / | Intravenous drip in other groups at 3 hours before LPS perfusion |
| 2 | PBS | 6 | i.v. | N/A | 2.5 | / | Intravenous drip at 3 hours before LPS perfusion |
| 3 | DEX | 6 | p.o. | 0.4 | 2.5 | 1 | Intraperitoneal administration at 16 hours and 3 hours before LPS perfusion |
| 4 | ZD004 | 6 | i.v. | 2 | 2.5 | 5 | Intravenous drip at 3 hours before LPS perfusion |
| 5 | ZD018 | 6 | i.v. | 2 | 2.5 | 5 | Intravenous drip at 3 hours before LPS perfusion |

TABLE 1-continued

Animal grouping and dosage regimen

| Group | Test substance | Number of rats | Routes of administration | Concentration mg/mL | Dosage mL/kg | Dosage mg/kg | Dosage regimen |
|---|---|---|---|---|---|---|---|
| 6 | ZD018 | 6 | i.v. | 0.4 | 2.5 | 1 | Intravenous drip at 3 hours before LPS perfusion |
| 7 | ZD018 | 6 | i.v. | 0.08 | 2.5 | 0.2 | Intravenous drip at 3 hours before LPS perfusion |

Note:
PBS: phosphate buffer;
DEX: dexamethasone;
ZD004: slit2D2-HSA;
ZD018: slit2D2(C-S)-HSA;
N/A represents Not Applicable.

2.3 Establishment of Animal Models

Except for group 1, all other groups were received pulmonary perfusion of lipopolysaccharide. Animals were anesthetized by 3-5% isoflurane, and 100 μl of LPS solution (1 mg/ml) was introduced into rat trachea with a microatomizer intubation, and after 4 hours, the animals were killed with chloral hydrate (750 mg/kg). The lungs were gently perfused three times in situ with 4 ml of PBS+1% albumin. After lavage, bronchoalveolar lavage fluid (BALF) was preserved in ice, and then the number of eosinophils (EOS), macrophages (Mac), neutrophils (Neu), lymphocytes (Lym) and the total number of cells were measured.

2.4 Experimental Results

Figure 4:
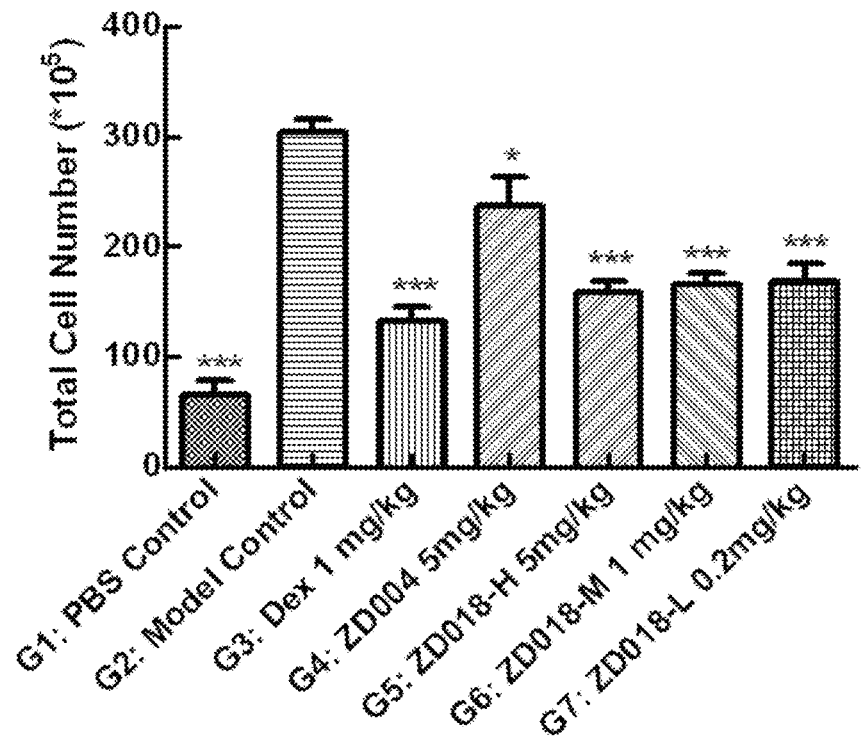
FIG. 4 illustrates a graph showing the results of an experiment for inhibiting inflammatory cell migration by the recombinant Slit2D2(C386S)-HSA fusion protein provided by the embodiments of the present invention, wherein G1 represents group 1, G2 represents group 2, and so on, and other groups are compared with the G2 group, * represents $p<0.001$,  represents $p<0.01$, and * represents $p<0.05$.

In this study, pharmacodynamic results were shown in FIG. 4, group 2 was LPS model group, and the total number of cells was increased. The number of neutrophils and the total number of cells were significantly reduced at a dose of 1 mg/kg of the positive control dexamethasone. Compared with the model group, the fusion protein Slit2D2(C386S)-HSA significantly inhibited the increase of cell number and the number of neutrophils was significantly controlled at the test doses of 5 mg/kg, 1 mg/kg and 0.2 mg/kg. Meanwhile, the efficacy of Slit2D2(C386S)-HSA was superior to Slit2D2-HSA recombinant protein at 5 mg/kg dose.

In models of acute lung injury, inflammatory cell infiltration was the most important factor causing tissue damage, so the above results indicated that Slit2D2 (C386S)-HSA fusion protein could protect lung tissue structure and function by significantly inhibiting the inflammatory cells from infiltrating into lung.

Example 3 Evaluation of Efficacy of Fusion Protein Slit2D2(C386S)-HSA in the Mouse Models of Asthma 3.1. Materials, Environment and Facilities
Experimental animals: BALB/c
Prior treatment: no
Gender: Female
Age: 6-7 weeks
Breeder/supplier: Beijing Weitong Lihua Experimental Animal Co., Ltd.
Testing facility: Shanghai PengLi Biological Company
Adaption: not less than 7 days
Room: SPF room
Room temperature: 20-26° C.
Relative humidity of room: 40-70%
Photoperiod: 12 hours of light (08:00-20:00) and 12 hours of darkness
Animal feeding: Treatment group 3~4/cage 3.2 Animal Grouping and Dosage Regimen The test design and dosage regimen of animal grouping are shown in Table 2.

TABLE 2

Animal grouping and dosage regimen

| Grouping | Drug | Number of animals | Routes of administration | Concentration mg/mL | Dosage mL/kg | Dosage mg/kg |
|---|---|---|---|---|---|---|
| G1-sham control (Blank group) | / | 10 | i.p. | N/A | 10 | N/A |
| G2-Vehicle (Control group) | PBS | 10 | i.p. | N/A | 10 | N/A |
| G3-ZD018 | ZD018* | 10 | i.p. | 5.12 | 10 | 1 |
| G4-dex | dexamethasone | 10 | p.o. | 0.1 | 10 | 1 |

Note:
ZD018: Slit2D2(386S)-HSA 3.3 Establishment of Animal Models 3.3.1 Sensitization of the Asthma Models On the first day and the 14th day of the experiment, the asthma models were sensitized by intraperitoneal injection, and the asthma group was given sensitization solution containing 20 μg of ovalbumin and 2 mg of alum suspension each time. The normal group did not receive any treatment.

3.3.2 On the days 28, 29 and 30, the mice of 2-4 groups were stimulated with aerosol, which included dissolving 100 mg OVA in 10 ml PBS and adding 5 μl Triton X-100, and atomized by atomizing inhalation facility (Buxco) for 30 minutes, and then the nebulizer was turned off. Finally, the mice were kept in the inhalation box for additional 7 minutes, and following by being taken out. The negative control mice were exposed in aerosolized PBS for 30 minutes.

3.3.3 Administration

Group 1 (PBS control group) were injected intraperitoneally with PBS at 2 hours before PBS sensitization on the days 28, 29 and 30. Group 2 (OVA control group) were injected intraperitoneally with PBS at 2 hours before OVA sensitization on the days 28, 29 and 30. Group 3 were injected intraperitoneally with ZD018 at 2 hours before OVA sensitization on the days 28, 29 and 30. Group 4 were intragastrically administrated with dexamethasone at 2 hours before OVA sensitization on the days 28, 29 and 30.

3.4 Test for Enhanced Pause (Penh)

On the 31st (24 hours after the last challenge), the Penh of mice were detected with a Buxco mouse non-invasive pulmonary function instrument. The change of Penh was determined after atomization stimulating of 300 µl doubling concentration of methacholine (Mch). The stimulating concentrations from low to high were 0, 0.78, 1.56, 3.125, 6.25, 12.5, 25 and 50 g/L, respectively. The mean value of Penh was recorded at each stimulating concentration level of Mch. The Penh value at each stimulating concentration of Mch was converted to a percentage of the Penh value at the time of the stimulating normal saline (The Penh value stimulated by Mch/The Penh value stimulated by normal saline, 100%), and represented by penh %, which was used as an evaluation index for mice airway response.

3.5 The observation of airway inflammation: the cytological examination of bronchoalveolar lavage and bronchoalveolar lavage fluid (BALF).

3.6 IL-13 and IL-5 cytokine levels in bronchoalveolar lavage fluid (BALF) were tested with Elisa Kit (R&D, USA).

3.7 Experimental Results

Figure 5:
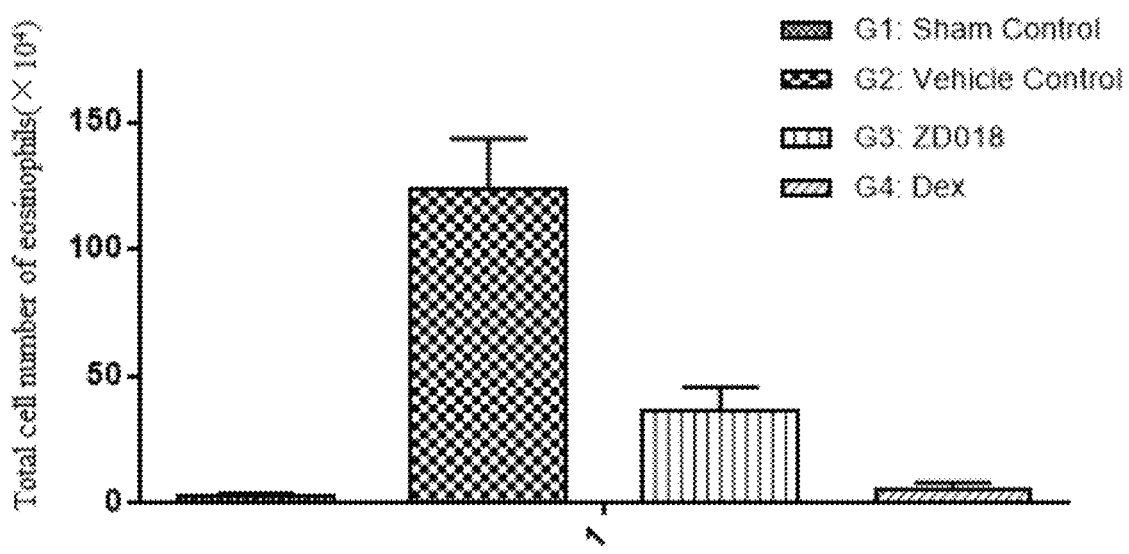
FIG. 5 illustrates a graph showing the results of inhibiting the accumulation of eosinophils in lung fluid by the recombinant Slit2D2(C386S)-HSA fusion protein provided by the embodiments of the present invention.
Figure 6:
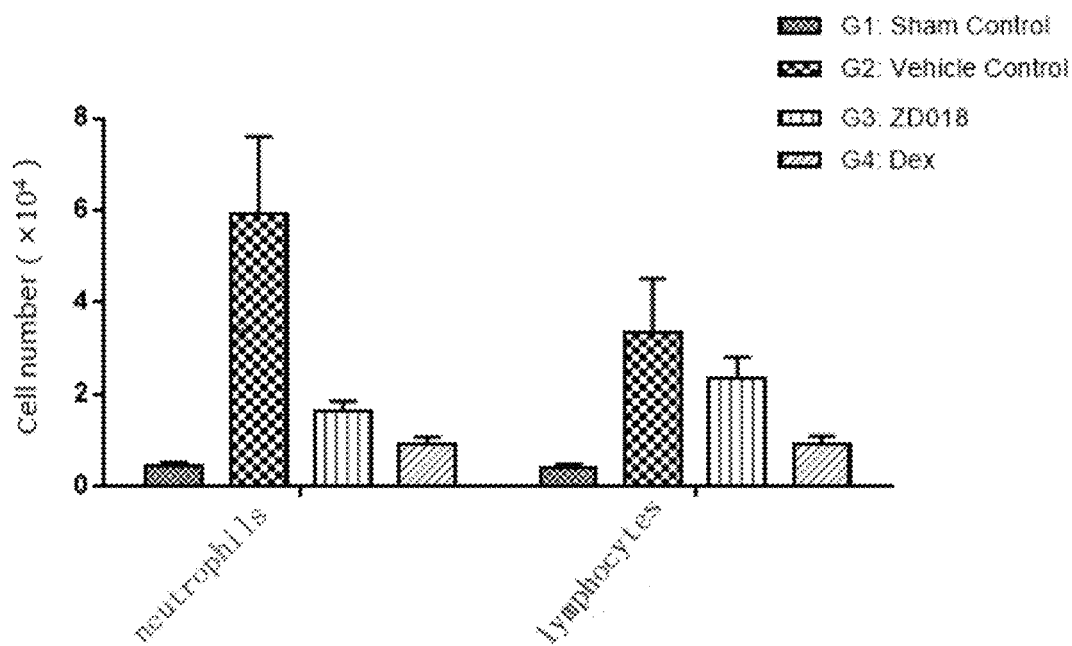
FIG. 6 illustrates a graph showing the results of inhibiting the accumulation of neutrophils and lymphocytes in lung fluid by the recombinant Slit2D2(C386S)-HSA fusion protein provided by the embodiments of the present invention.

Eosinophils are universally recognized as the main effector cells in asthma diseases in the medical field. Whether it can effectively inhibit this eosinophil is the key to evaluating the efficacy of a drug. In the mouse models of asthma, bronchoalveolar lavage fluid (BALF) was collected after experiment, and the inflammatory cells were counted. The results are shown in FIG. 5, after administration, the Slit2D2 (C386S)-HSA recombinant protein can significantly inhibit the accumulation of eosinophils in alveolar fluid. Meanwhile, as shown in FIG. 6, the Slit2D2(C386S)-HSA recombinant protein can also inhibit the accumulation of neutrophils and lymphocytes in alveolar fluid, which shows that this recombinant protein has significant drug effect.

Figure 7:
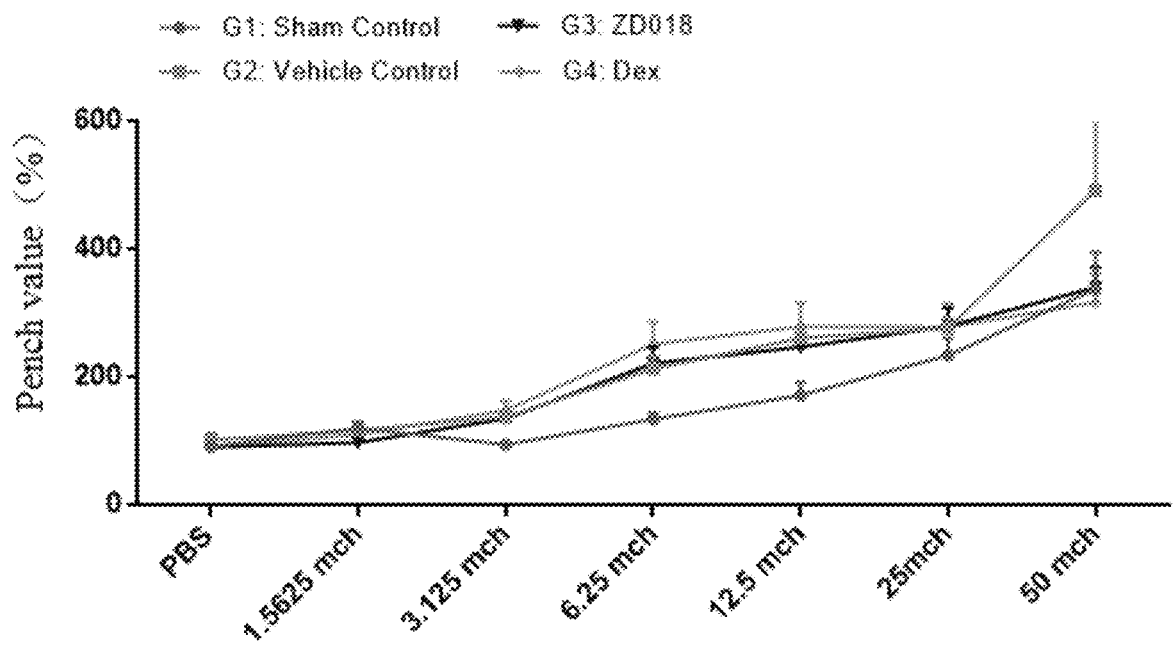
FIG. 7 illustrates a graph showing the results of detecting the function of the exhaled pause (Penh) function of the lung function of the mouse models of asthma provided by the embodiments of the present invention.

By the detection of the enhanced pause (Penh) function, the results were shown in FIG. 7, which shows the Slit2D2 (C386S)-HSA recombinant protein can effectively inhibit the pench index stimulated by methacholine (Mch). These results indicated: after treatment of asthma with Slit2D2 (C386S)-HSA recombinant protein, its lung function was good compared with the control group G2.

Figure 8:
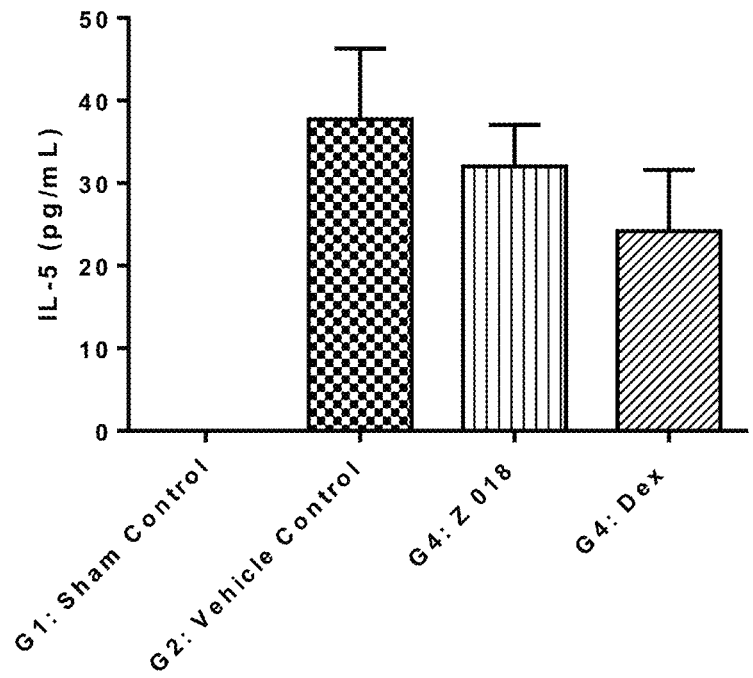
FIG. 8 illustrates a graph showing the results of detecting IL-5 cytokine levels of the bronchoalveolar lavage fluid (BALF) in the mouse models of asthma provided by the embodiments of the present invention.
Figure 9:
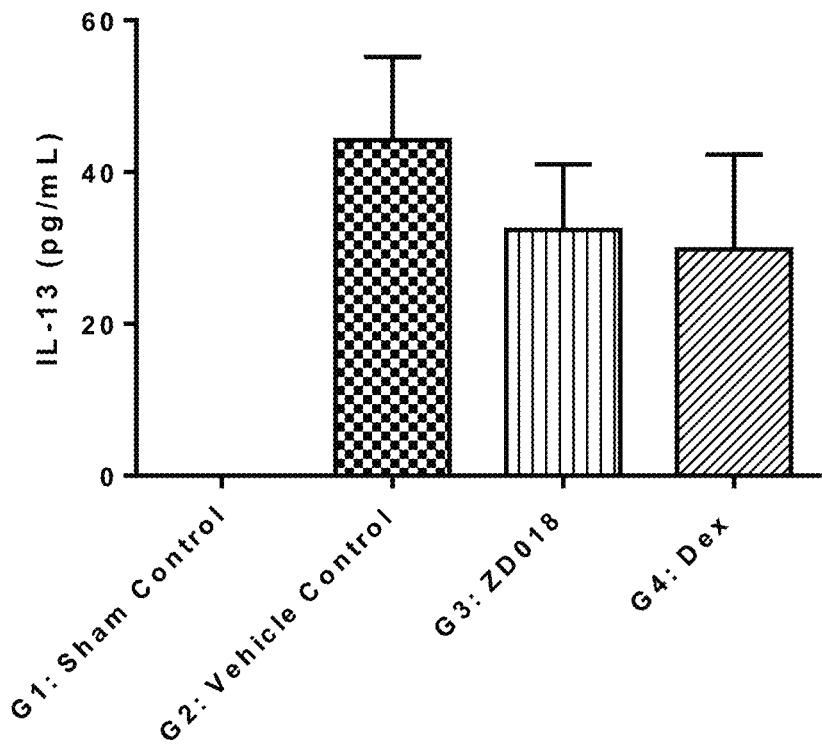
FIG. 9 illustrates a graph showing the results of detecting IL-13 cytokine levels of the bronchoalveolar lavage fluid (BALF) in the mouse models of asthma provided by the embodiments of the present invention.

The levels of IL-13 and IL-5 cytokine were detected in bronchoalveolar lavage fluid (BALF), IL-13 and IL-5 were important inflammatory factors in the asthma models, and play key role in the occurrence and development of disease. The results are shown in FIG. 8-9. The results indicates that the Slit2D2(C386S)-HSA recombinant protein can inhibit the levels of inflammatory cytokines IL-13 and IL-5 in the foaming solution of mouse models of asthma.

The above is only the preferred embodiment of the present invention, and is not intended to limit the present invention. Any modifications, equivalent substitutions, etc., made within the spirit and scope of the present invention, are intended to be included within the scope of the present invention.

The invention claimed is:

1. A method for treating asthma comprising a step of administering a pharmaceutical composition containing an effective amount of a fusion protein, wherein the fusion protein comprising the second domain (D2 domain) of Slit2 protein and Human Serum Albumin (HSA), and the cysteine in the D2 domain of the Slit2 protein, corresponding to the position 386 of the Slit2 protein, is mutated to serine (C386S); wherein the D2 domain of the Slit2 protein consists of the sequence as shown in SEQ ID NO: 1.

2. The method of claim 1, wherein the fusion protein has the following structure: Slit2D2 (C386S)-HSA, or HSA-Slit2D2 (C386S), wherein "-" represents a chemical bond or a linker.

3. The method of claim 1, wherein the fusion protein consists of the D2 domain of the Slit2 protein and HSA as shown in SEQ ID NO 2.

* * * * *

```
                      SEQUENCE LISTING

<160> NUMBER OF SEQ ID NOS: 3

<210> SEQ ID NO 1
<211> LENGTH: 209
<212> TYPE: PRT
<213> ORGANISM: Artificial
<220> FEATURE:
<223> OTHER INFORMATION: D2 domain of Slit2 protein

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Ser Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160
```

-continued

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser

<210> SEQ ID NO 2
<211> LENGTH: 794
<212> TYPE: PRT
<213> ORGANISM: Artificial
<220> FEATURE:
<223> OTHER INFORMATION: Slit2D2(C386S)-HSA fusion protein

<400> SEQUENCE: 2

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Ser Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser Asp Ala His Lys Ser Glu Val Ala His Arg Phe Lys Asp Leu Gly
    210                 215                 220

Glu Glu Asn Phe Lys Ala Leu Val Leu Ile Ala Phe Ala Gln Tyr Leu
225                 230                 235                 240

Gln Gln Cys Pro Phe Glu Asp His Val Lys Leu Val Asn Glu Val Thr
                245                 250                 255

Glu Phe Ala Lys Thr Cys Val Ala Asp Glu Ser Ala Glu Asn Cys Asp
            260                 265                 270

Lys Ser Leu His Thr Leu Phe Gly Asp Lys Leu Cys Thr Val Ala Thr
        275                 280                 285

Leu Arg Glu Thr Tyr Gly Glu Met Ala Asp Cys Cys Ala Lys Gln Glu
    290                 295                 300

```
Pro Glu Arg Asn Glu Cys Phe Leu Gln His Lys Asp Asp Asn Pro Asn
305                 310                 315                 320

Leu Pro Arg Leu Val Arg Pro Glu Val Asp Val Met Cys Thr Ala Phe
            325                 330                 335

His Asp Asn Glu Glu Thr Phe Leu Lys Lys Tyr Leu Tyr Glu Ile Ala
        340                 345                 350

Arg Arg His Pro Tyr Phe Tyr Ala Pro Glu Leu Leu Phe Phe Ala Lys
    355                 360                 365

Arg Tyr Lys Ala Ala Phe Thr Glu Cys Cys Gln Ala Ala Asp Lys Ala
370                 375                 380

Ala Cys Leu Leu Pro Lys Leu Asp Glu Leu Arg Asp Glu Gly Lys Ala
385                 390                 395                 400

Ser Ser Ala Lys Gln Arg Leu Lys Cys Ala Ser Leu Gln Lys Phe Gly
            405                 410                 415

Glu Arg Ala Phe Lys Ala Trp Ala Val Ala Arg Leu Ser Gln Arg Phe
        420                 425                 430

Pro Lys Ala Glu Phe Ala Glu Val Ser Lys Leu Val Thr Asp Leu Thr
    435                 440                 445

Lys Val His Thr Glu Cys Cys His Gly Asp Leu Leu Glu Cys Ala Asp
450                 455                 460

Asp Arg Ala Asp Leu Ala Lys Tyr Ile Cys Glu Asn Gln Asp Ser Ile
465                 470                 475                 480

Ser Ser Lys Leu Lys Glu Cys Cys Glu Lys Pro Leu Leu Glu Lys Ser
            485                 490                 495

His Cys Ile Ala Glu Val Glu Asn Asp Glu Met Pro Ala Asp Leu Pro
        500                 505                 510

Ser Leu Ala Ala Asp Phe Val Glu Ser Lys Asp Val Cys Lys Asn Tyr
    515                 520                 525

Ala Glu Ala Lys Asp Val Phe Leu Gly Met Phe Leu Tyr Glu Tyr Ala
530                 535                 540

Arg Arg His Pro Asp Tyr Ser Val Val Leu Leu Leu Arg Leu Ala Lys
545                 550                 555                 560

Thr Tyr Glu Thr Thr Leu Glu Lys Cys Cys Ala Ala Ala Asp Pro His
            565                 570                 575

Glu Cys Tyr Ala Lys Val Phe Asp Glu Phe Lys Pro Leu Val Glu Glu
        580                 585                 590

Pro Gln Asn Leu Ile Lys Gln Asn Cys Glu Leu Phe Glu Gln Leu Gly
    595                 600                 605

Glu Tyr Lys Phe Gln Asn Ala Leu Leu Val Arg Tyr Thr Lys Lys Val
610                 615                 620

Pro Gln Val Ser Thr Pro Thr Leu Val Glu Val Ser Arg Asn Leu Gly
625                 630                 635                 640

Lys Val Gly Ser Lys Cys Cys Lys His Pro Glu Ala Lys Arg Met Pro
            645                 650                 655

Cys Ala Glu Asp Tyr Leu Ser Val Val Leu Asn Gln Leu Cys Val Leu
        660                 665                 670

His Glu Lys Thr Pro Val Ser Asp Arg Val Thr Lys Cys Cys Thr Glu
    675                 680                 685

Ser Leu Val Asn Arg Arg Pro Cys Phe Ser Ala Leu Glu Val Asp Glu
690                 695                 700

Thr Tyr Val Pro Lys Glu Phe Asn Ala Glu Thr Phe Thr Phe His Ala
705                 710                 715                 720

Asp Ile Cys Thr Leu Ser Glu Lys Glu Arg Gln Ile Lys Lys Gln Thr
```

```
                        725                 730                 735
Ala Leu Val Glu Leu Val Lys His Lys Pro Lys Ala Thr Lys Glu Gln
                740                 745                 750

Leu Lys Ala Val Met Asp Asp Phe Ala Ala Phe Val Glu Lys Cys Cys
            755                 760                 765

Lys Ala Asp Asp Lys Glu Thr Cys Phe Ala Glu Glu Gly Lys Lys Leu
    770                 775                 780

Val Ala Ser Gln Ala Ala Leu Gly Leu
785                 790

<210> SEQ ID NO 3
<211> LENGTH: 2385
<212> TYPE: DNA
<213> ORGANISM: Artificial
<220> FEATURE:
<223> OTHER INFORMATION: Nucleotide of Slit2D2(C386S)-HSA

<400> SEQUENCE: 3
ttgcactgcc ctgccgcctg tacctgtagc aacaatatcg tagactgtcg tgggaaaggt      60
ctcactgaga tccccacaaa tcttccagag accatcacag aaatacgttt ggaacagaac     120
acaatcaaag tcatccctcc tggagctttc tcaccatata aaaagcttag acgaattgac     180
ctgagcaata atcagatctc tgaacttgca ccagatgctt tccaaggact acgctctctg     240
aattcacttg tcctctatgg aaataaaatc acagaactcc ccaaaagttt atttgaagga     300
ctgttttcct tacagctcct attattgaat gccaacaaga taaacagtct tcgggtagat     360
gcttttcagg atctccacaa cttgaacctt ctctccctat atgacaacaa gcttcagacc     420
atcgccaagg ggaccttttc acctcttcgg gccattcaaa ctatgcattt ggcccagaac     480
ccctttattt gtgactgcca tctcaagtgg ctagcggatt atctccatac caacccgatt     540
gagaccagtg gtgcccgttg caccagcccc cgccgcctgg caaacaaaag aattggacag     600
atcaaaagca gaaaattccg ttgttcagat gcacacaaga gtgaggttgc tcatcggttt     660
aaagatttgg gagaagaaaa tttcaaagcc ttggtgttga ttgcctttgc tcagtatctt     720
cagcagtgtc catttgaaga tcatgtaaaa ttagtgaatg aagtaactga atttgcaaaa     780
acatgtgttg ctgatgagtc agctgaaaat tgtgacaaat cacttcatac ccttttttgga    840 gacaaattat gcacagttgc aactcttcgt gaaacctatg gtgaaatggc tgactgctgt    900
gcaaaacaag aacctgagag aaatgaatgc ttcttgcaac acaaagatga caacccaaac    960 ctccccccgat tggtgagacc agaggttgat gtgatgtgca ctgcttttca tgacaatgaa    1020
gagacatttt tgaaaaaata cttatatgaa attgccagaa gacatcctta cttttatgcc    1080
ccggaactcc ttttctttgc taaaaggtat aaagctgctt ttacagaatg ttgccaagct    1140
gctgataaag ctgcctgcct gttgccaaag ctcgatgaac ttcgggatga agggaaggct    1200
tcgtctgcca aacagagact caagtgtgcc agtctccaaa aatttggaga aagagctttc    1260
aaagcatggg cagtagctcg cctgagccag agatttccca agctgagtt tgcagaagtt    1320 tccaagttag tgacagatct taccaaagtc cacacggaat gctgccatgg agatctgctt    1380
gaatgtgctg atgacagggc ggaccttgcc agtatatct gtgaaaatca agattcgatc    1440
tccagtaaac tgaaggaatg ctgtgaaaaa cctctgttgg aaaaatccca ctgcattgcc    1500
gaagtggaaa atgatgagat gcctgctgac ttgccttcat agctgctga ttttgttgaa    1560 agtaaggatg tttgcaaaaa ctatgctgag gcaaaggatg tcttcctggg catgttttg    1620 tatgaatatg caagaaggca tcctgattac tctgtcgtgc tgctgctgag acttgccaag    1680
```

```
acatatgaaa ccactctaga gaagtgctgt gccgctgcag atcctcatga atgctatgcc    1740
aaagtgttcg atgaatttaa acctcttgtg gaagagcctc agaatttaat caaacaaaat    1800
tgtgagcttt ttgagcagct tggagagtac aaattccaga atgcgctatt agttcgttac    1860
accaagaaag taccccaagt gtcaactcca actcttgtag aggtctcaag aaacctagga    1920
aaagtgggca gcaaatgttg taaacatcct gaagcaaaaa gaatgccctg tgcagaagac    1980
tatctatccg tggtcctgaa ccagttatgt gtgttgcatg agaaaacgcc agtaagtgac    2040
agagtcacca aatgctgcac agaatccttg gtgaacaggc gaccatgctt ttcagctctg    2100
gaagtcgatg aaacatacgt tcccaaagag tttaatgctg aaacattcac cttccatgca    2160
gatatatgca cactttctga gaaggagaga caaatcaaga aacaaactgc acttgttgag    2220
ctcgtgaaac acaagcccaa ggcaacaaaa gagcaactga aagctgttat ggatgatttc    2280
gcagcttttg tagagaagtg ctgcaaggct gacgataagg agacctgctt tgccgaggag    2340
ggtaaaaaac ttgttgctgc aagtcaagct gccttaggct tataa                    2385
```